(12) United States Patent
Machida et al.

(10) Patent No.: US 8,076,302 B2
(45) Date of Patent: Dec. 13, 2011

(54) PYRIMIDINE NUCLEOSIDE DERIVATIVES AND SALTS THEREOF

(75) Inventors: Haruhiko Machida, Tokyo (JP); Masaichi Yamamoto, Tokyo (JP)

(73) Assignee: aRigen Pharmaceuticals, Inc., Tokyo (JP)

( * ) Notice: Subject to any disclaimer, the term of this patent is extended or adjusted under 35 U.S.C. 154(b) by 251 days.

(21) Appl. No.: 12/438,108

(22) PCT Filed: Feb. 15, 2007

(86) PCT No.: PCT/JP2007/052758
§ 371 (c)(1),
(2), (4) Date: Feb. 19, 2009

(87) PCT Pub. No.: WO2008/099492
PCT Pub. Date: Aug. 21, 2008

(65) Prior Publication Data
US 2010/0234405 A1    Sep. 16, 2010

(51) Int. Cl.
*C07H 19/09* (2006.01)
*A61K 31/7072* (2006.01)

(52) U.S. Cl. ......... 514/32; 514/274; 536/27.4; 544/309; 544/311; 544/312; 544/314

(58) Field of Classification Search ................. 536/27.4; 544/309, 311, 312, 314; 514/32, 274
See application file for complete search history.

(56) References Cited

U.S. PATENT DOCUMENTS

| | | | |
|---|---|---|---|
| 4,386,076 A | 5/1983 | Machida et al. | |
| 4,542,210 A | 9/1985 | Sakata et al. | |
| 5,446,031 A | 8/1995 | Sakata et al. | |

FOREIGN PATENT DOCUMENTS

| | | |
|---|---|---|
| EP | 31128 A1 | 7/1981 |
| EP | 74101 A1 | 3/1983 |
| EP | 572669 A1 | 12/1993 |
| JP | 56-87599 A | 7/1981 |
| JP | 58-43993 A | 3/1983 |
| JP | 4-505920 A | 10/1992 |
| WO | WO 90/15064 A1 | 12/1990 |
| WO | WO 92/19638 A | 11/1992 |

OTHER PUBLICATIONS

Razonable et al., PubMed Abstract (Herpes 10(3):60-5), Dec. 2003.*
Douglas, Jr. Introduction to Viral Diseases, Cecil Textbook of Medicine, 20$^{th}$ Edition, vol. 2, pp. 1739-1747, 1996.*
Goff, PubMed Abstract (J Gene Med. 3(6):517-28) Nov.-Dec. 2001.*
Bosseray et al., PubMed Abstract (Pathol. Biol. 50(8):483-92), Oct. 2002.*

Kano, F. et al., 5'-O-alkyl and acyl prodrugs of 1-β-D-arabinofuranosyl-E-5-(2-bromovinyl) uracil, Antiviral Chemistry & Chemotherapy, 1994, vol. 5, No. 2, pp. 74-82.
Ashida, Noriyuki et al., Metabolism of 5'-ether prodrugs of 1-β-D-arabinofuranosyl-E-5-(2-bromovinyl) uracil in rats, Biochemical Pharmacology, 1993, vol. 46, No. 12, pp. 2201-2207.
Reefschlaeger, J. et al., Antiherpes activity of (E)-5-(2-bromovinyl)- and 5-vinyl-1-β-D-arabinofuranosyluracil and some other 5-substituted uracil arabinosyl nucleosides in two different cell lines, Antiviral Research, 1983, vol. 3, No. 3, pp. 175-187.
Machida, H. et al., In vitro anti-herpesvirus activities of 5-substituted 2'-deoxy-2' methylidene pyrimidine nucleosides, Antiviral Chemistry & Chemotherapy, 1993, vol. 4, No. 1, pp. 11-17.
Yu, Chung-Shan et al., Synthesis of (E)-5-(2-radio-iodovinyl) arabinosyl uridine analog for probing HSV-1 thymidine kinase gene, Chemistry Letters, 2005, vol. 34, No. 10, pp. 1390-1391.
Yu, Chung-Shan et al., Syntheses of 5-fluoro and (E)-5-(2-fluorovinyl) arabinosyl uridine analogues as potential probes for the HSV-1 thymidine kinase gene, Synthesis, 2006, No. 22, pp. 3835-3840.
Kulikowski, T. et al., Pyrimidine arabinofuranosyl nucleosides with 5-substituted long, branched and unsaturated chains: synthesis and antiherpes properties, Nucleic Acids Symposium Series, 1981, vol. 9, pp. 103-106.

* cited by examiner

*Primary Examiner* — Deepak Rao
(74) *Attorney, Agent, or Firm* — Harness, Dickey & Pierce, P.L.C.; Michael E. Hilton

(57) ABSTRACT

A novel pyrimidine nucleoside derivative represented by the following formula (1) and a salt thereof, as well as a pharmaceutical composition comprising the same as an active ingredient have excellent antiviral properties and are useful as antiviral therapeutic agents:

[Formula 1]

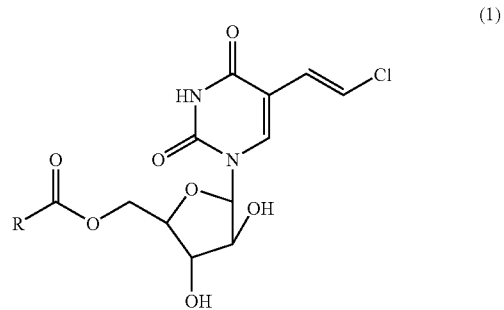

(1)

[wherein R represents a nitrogen-containing heterocyclic ring which may have any one of a $C_1$-$C_3$ alkyl group or a $C_1$-$C_3$ alkoxy group as a substituent, or a $C_1$-$C_6$ alkyl group which has one primary amino group as a substituent].

13 Claims, 1 Drawing Sheet

PYRIMIDINE NUCLEOSIDE DERIVATIVES AND SALTS THEREOF

CROSS-REFERENCE TO RELATED APPLICATIONS

This application is a 371 U.S. National Stage of International Application No. PCT/JP2007/052758, filed Feb. 15, 2007. The disclosure of the above application is entirely incorporated herein by reference.

TECHNICAL FIELD

The present invention relates to novel pyrimidine nucleoside derivatives having excellent antiviral properties and salts thereof, as well as applications of these compounds.

BACKGROUND ART

"Herpes virus" comes from the ancient Greek meaning "to creep or crawl while hiding itself." The feature of this virus is that once it has infected patients, the virus continues to hide in their ganglia even after symptoms have dissipated, and becomes active again upon reduction of the patients' immunity.

At present, 8 types of herpes viruses are known to infect humans: herpes simplex virus type 1 (HSV-1) which causes gingivostomatitis, keratitis, pharyngitis, herpes labialis, etc.; herpes simplex virus type 2 (HSV-2) which is responsible for genital herpes infections; varicella-zoster virus (VZV); cytomegalo virus (CMV) which causes retinitis, hepatitis, interstitial pneumonia, etc.; EB virus (EBV) which is responsible for infectious mononucleosis; human herpes virus 6 (HHV-6) which causes exanthema subitum; human herpes virus 7 (HHV-7); and human herpes virus 8 (HHV-8) which is responsible for Kaposi's sarcoma seen in AIDS patients.

Herpes virus infections are characterized by persistent infection (latent infection) in the body (mainly in ganglia) following primary infection. Except for VZV and HHV-6 cases, primary infection is often inapparent infection. After primary infection, regardless of whether it is apparent or inapparent, the viruses establish latent infection in trigeminal and/or sacral ganglia, and they further cause blisters at specific skin sites such as areas around the lips and genitals (recurrent infection) when the viruses become active again due to fatigue, pregnancy, injury, febrile diseases and other causes.

The incidence rate of herpes zoster is reported to be 300 patients per year per 100,000 adults. Herpes zoster patients are numerous particularly among the elderly (50 to 79 years old), and tend to slightly increase. In recent years, there has been an increasing number of patients who develop herpes zoster at younger ages and repeatedly. In patients whose pain persists for a month after developing the disease, the pain disappears within 3 months in half of such patients, but it persists for 3 months or longer in the remaining half of the patients, 20% of which will have pain persisting for longer than a year (postherpetic neuralgia).

DISCLOSURE OF THE INVENTION

Problems to be Solved by the Invention

Many antibiotics are known for bacterial infections, whereas there are few antiviral agents effective against virus infections.

Sorivudine [i.e., 1-β-D-arabinofuranosyl-(E)-5-(2-bromovinyl)uracil] has a cytostatic effect on herpes simplex virus type 1 (HSV-1) and varicella-zoster virus (VZV), and is also known as a compound whose cytotoxicity is extremely low because it is not phosphorylated in uninfected cells (Patent Document 1). Moreover, as an external formulation for HSV-1 infection in mice, sorivudine is also reported to be as useful as acyclovir (i.e., 9-[(2-hydroxyethoxy)methyl]guanine) which is a representative antiviral drug and is regarded as being effective for treatment of herpes virus infections and other purposes (Non-patent Document 1). Further, CVAU [i.e., 1-β-D-arabinofuranosyl-(E)-5-(2-chlorovinyl)uracil, 5-chlorovinyl-araU] is also known to have the same activity as sorivudine (Patent Document 1). However, there is still a demand for the development of antiviral therapeutic agents which are highly effective in in vivo tests and are expected to have a higher therapeutic effect.

Patent Document 1: JP 57-48160 B
Non-patent Document 1: Antiviral Research, 21, 47-57, 1993

The object of the present invention is to provide a compound useful as an antiviral therapeutic agent which has excellent antiviral properties, and a pharmaceutical agent containing the same.

Means for Solving the Problems

As a result of extensive and intensive efforts, the inventors of the present invention have found that a novel pyrimidine nucleoside derivative represented by the following formula (1) has an excellent anti-herpesvirus effect. This finding led to the completion of the present invention.

The present invention is directed to the following inventions.

1. A novel pyrimidine nucleoside derivative represented by formula (1) and a salt thereof:

[Formula 1]

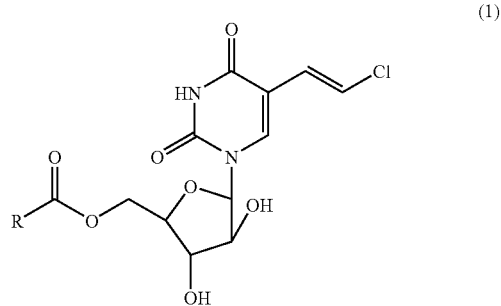

[wherein R represents a nitrogen-containing heterocyclic ring which may have any one of a $C_1$-$C_3$ alkyl group or a $C_1$-$C_3$ alkoxy group as a substituent, or a $C_1$-$C_6$ alkyl group which has one primary amino group as a substituent].

2. A pharmaceutical composition, which comprises a compound represented by formula (1) or a salt thereof as an active ingredient together with a pharmaceutically acceptable carrier or diluent.

3. An antiviral agent, which comprises a compound represented by formula (1) or a salt thereof as an active ingredient.

4. A method for treating a virus infection, which comprises administering a therapeutically effective amount of at least one compound represented by formula (1) or salt thereof to a patient in need of treatment.

5. Use of a compound represented by formula (1) or a salt thereof in the manufacture of a pharmaceutical preparation for treating a patient with a virus infection.

Advantages of the Invention

The novel pyrimidine nucleoside derivatives of the present invention and salts thereof have excellent antiviral effects and are useful as antiviral agents (therapeutic agents for virus infections).

BEST MODE FOR CARRYING OUT THE INVENTION

Figure 1:
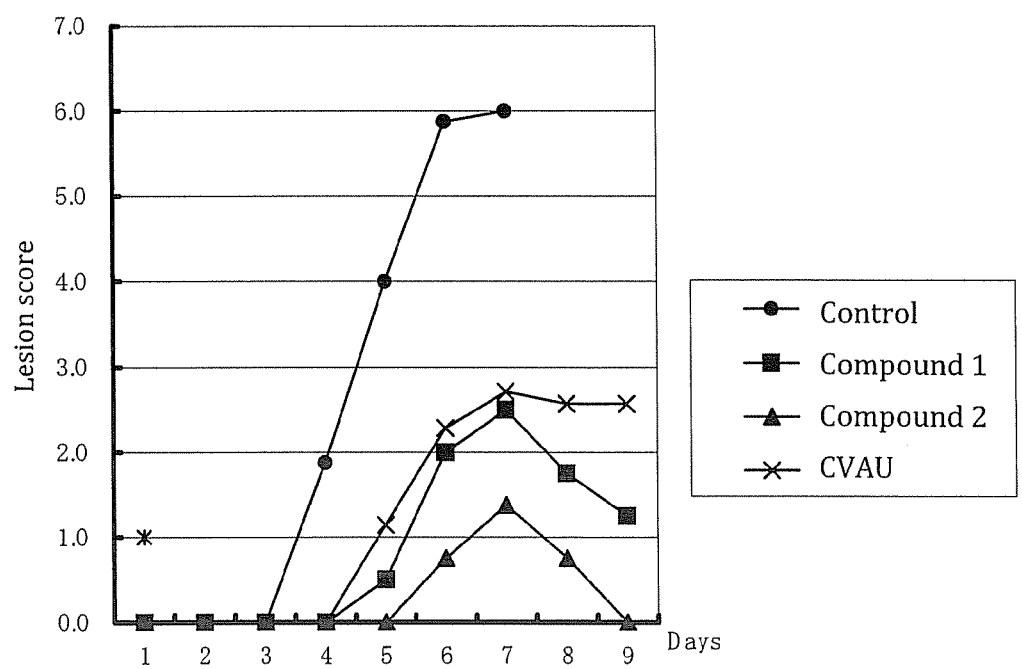
FIG. 1 is a graph showing the time course of changes in average lesion scores during antiviral test.

The pyrimidine nucleoside derivatives of the present invention are novel compounds having a chemical structure represented by the above formula (1), wherein R represents a nitrogen-containing heterocyclic ring which may have any one of a $C_1$-$C_3$ alkyl group or a $C_1$-$C_3$ alkoxy group as a substituent, or a $C_1$-$C_6$ alkyl group which has one primary amino group as a substituent. The compounds of the present invention represented by the above formula (1) and salts thereof have various structural isomers and stereoisomers. All of these isomers also fall within the scope of the pyrimidine nucleoside derivatives of the present invention and salts thereof.

Preferred nitrogen-containing heterocyclic rings are piperidine (including positional isomers), pyridine (including positional isomers) and pyrimidine (including positional isomers), each of which may have any one of a $C_1$-$C_3$ alkyl group or a $C_1$-$C_3$ alkoxy group as a substituent.

Examples of a $C_1$-$C_3$ alkyl group which may be on the nitrogen-containing heterocyclic ring include a methyl group, an ethyl group, a propyl group and an isopropyl group, with a methyl group being preferred.

Examples of a $C_1$-$C_3$ alkoxy group which may be on the nitrogen-containing heterocyclic ring include a methoxy group, an ethoxy group, a propoxy group and an isopropoxy group, with a methoxy group being preferred.

Examples of a $C_1$-$C_6$ alkyl group in the $C_1$-$C_6$ alkyl group which has one primary amino group as a substituent include a methyl group, an ethyl group, a propyl group, an isopropyl group, a butyl group, an isobutyl group, an isopropylmethyl group (a 2-methylpropyl group), a n-pentyl group, a cyclopentyl group, an n-hexyl group and a cyclohexyl group, with an isopropylmethyl group (a 2-methylpropyl group) being preferred.

R is more preferably a 1-amino-2-methylpropyl group, a 4-piperidyl group, a N-methylpiperidyl group, a 2-pyridyl group, a 3-pyridyl group, a 4-pyridyl group or a 2-methoxy-5-pyrimidinyl group.

R is most preferably a 1-amino-2-methyl-propyl group or a 4-piperidyl group.

Salts of the pyrimidine nucleoside derivatives of the present invention may be any salts as long as they are pharmaceutically acceptable salts. Examples include mineral acid salts such as a hydrochloride salt, a hydrobromide salt, a sulfate salt, a nitrate salt and a phosphate salt, as well as organic acid salts such as an acetate salt, a propionate salt, a tartrate salt, a fumarate salt, a maleate salt, a malate salt, a citrate salt, a methanesulfonate salt, a paratoluenesulfonate salt and a trifluoroacetate salt. Moreover, the pyrimidine nucleoside derivatives of the present invention can be present in the form of solvates typified by hydrates, and such solvates typified by hydrates also fall within the scope of the present invention.

The novel pyrimidine nucleoside derivatives of the present invention and salts thereof can be prepared according to Reaction Scheme 1 or 2 shown below. In these schemes, formula (2) represents a pyrimidine nucleoside derivative of formula (1), in which the nitrogen atom(s) in the substituent R may be protected with a protecting group(s).

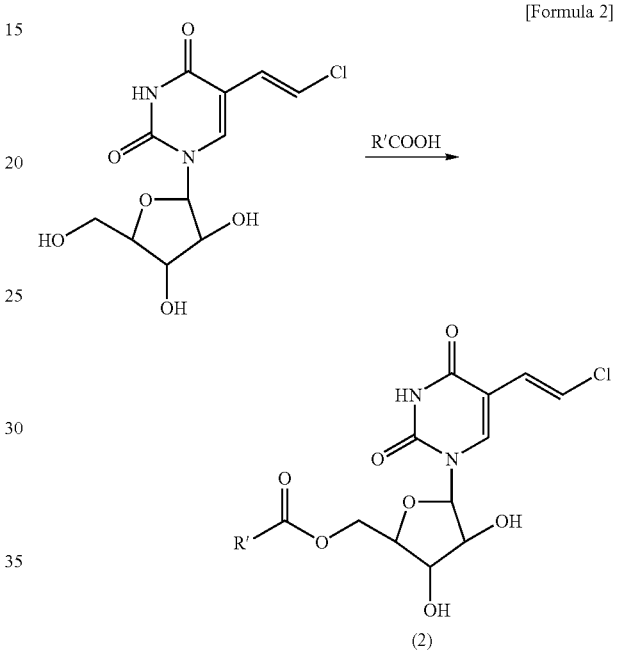

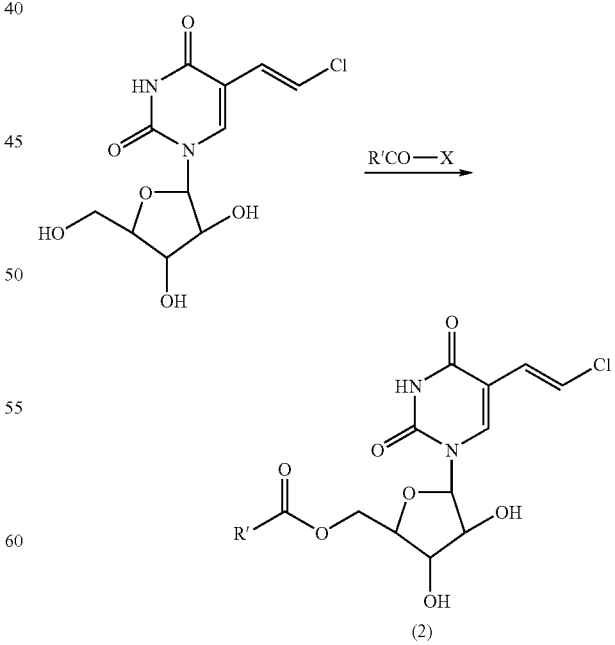

wherein R' represents piperidinecarboxylic acid whose nitrogen atom may be protected, pyridinecarboxylic acid whose nitrogen atom may be protected, pyrimidinecarboxylic acid whose nitrogen atoms may be protected, or a $C_1$-$C_6$ alkyl group which has one primary amino group as a substituent whose nitrogen atom may be protected. Protecting groups for nitrogen atoms are not limited in any way as long as they are conventionally known protecting groups, and suitable examples are those found in T. W. Greene, "Protective groups in Organic Synthesis", A Wiley-Interscience Publication, John-Wiley & Sons, New York, 1981, p. 218-287, as exemplified by a tert-butoxycarbonyl group (Boc).

(Scheme 1)

In this scheme, (E)-5-(2-chlorovinyl)-1-β-D-arabinofuranosyluracil may be reacted through condensation reaction with, e.g., piperidinecarboxylic acid whose nitrogen atom is protected, a $C_1$-$C_6$ alkyl group which has one primary amino group as a substituent whose nitrogen atom is protected, pyridinecarboxylic acid, or pyrimidinecarboxylic acid to thereby prepare a compound represented by formula (2).

The condensation reaction is not limited in any way as long as it is commonly used to prepare an ester from a carboxylic acid and an alcohol, as exemplified by a mixed acid anhydride method, a method using a condensing agent, etc.

In the case of using a mixed acid anhydride method, examples of a reagent used for mixed acid anhydride formation include isobutyl chlorocarbonate, pivaloyl chloride, etc. Likewise, examples of a base available for use include organic amines such as trimethylamine, triethylamine, tripropylamine, diisopropylethylamine, N-methylmorpholine, pyridine, 4-(N,N-dimethylamino)pyridine, lutidine and collidine, as well as inorganic bases such as sodium bicarbonate, sodium carbonate and potassium carbonate.

Examples of a reagent used as a condensing agent include 1,3-dicyclohexylcarbodiimide (DCC), 1-ethyl-3-(3-dimethylaminopropyl)carbodiimide hydrochloride (EDC), carbonyldiimidazole (CDI), and diphenylphosphorylazide (DPPA). Examples of a condensation aid include 1-hydroxybenzotriazole hydrate (HOBT), N-hydroxysuccinimide (HONSu), N-hydroxy-5-norbornene-2,3-dicarboxylic acid imide (HONB), and 4-dimethylaminopyridine (DMAP). Any solvent may be used as long as it is inert to the reaction, and examples include dichloromethane, chloroform, ethyl acetate, tetrahydrofuran (THF), dioxane, diethyl ether, benzene, toluene, N,N-dimethylformamide (DMF) and dimethyl sulfoxide (DMSO), which may be used either alone or in combination. The reaction temperature ranges from −30° C. to 100° C., preferably 0° C. to 30°, while the reaction time is 0.1 to 100 hours, preferably 1 to 20 hours. The compound of formula (2) prepared by this reaction may be isolated and purified as required, or may be used directly, without purification, for deprotection or salt formation described below.

In a case where the pyrimidine nucleoside derivative represented by formula (2) has a protecting group(s) on its nitrogen atom(s), a deprotecting reagent may be reacted to remove the protecting group(s) to thereby obtain a compound represented by formula (1). For example, when the protecting group is a tert-butoxycarbonyl group (Boc), any deprotecting reagent may be used as long as it is commonly used, and examples include mineral acids such as hydrochloric acid, hydrobromic acid, sulfuric acid, nitric acid and phosphoric acid, as well as organic acids such as trifluoroacetic acid, acetic acid, propionic acid, formic acid, methanesulfonic acid and paratoluenesulfonic acid.

Examples of a solvent available for use include dichloromethane, chloroform, ethyl acetate, tetrahydrofuran (THF), dioxane, diethyl ether, benzene, toluene, acetone, N,N-dimethylformamide (DMF), dimethyl sulfoxide (DMSO), methanol, ethanol and water, which may be used either alone or in combination. The reaction temperature ranges from −30° C. to 150° C., preferably 0° C. to 100° C., while the reaction time is 0.1 to 100 hours, preferably 1 to 40 hours.

(Scheme 2)

In this scheme, (E)-5-(2-chlorovinyl)-1-β-D-arabinofuranosyluracil may be reacted with an acid chloride (X=Cl) derived from, e.g., pyridinecarboxylic acid or pyrimidinecarboxylic acid in the presence of a base to thereby prepare a compound represented by formula (2).

Examples of a base available for use include organic amines such as trimethylamine, triethylamine, tripropylamine, diisopropylethylamine, N-methylmorpholine, pyridine, 4-(N,N-dimethylamino)pyridine, lutidine and collidine, as well as inorganic bases such as sodium bicarbonate, sodium carbonate and potassium carbonate. Any solvent may be used as long as it is inert to the reaction, and examples include dichloromethane, chloroform, ethyl acetate, tetrahydrofuran (THF), dioxane, diethyl ether, benzene, toluene, N,N-dimethylformamide (DMF) and dimethyl sulfoxide (DMSO), which may be used either alone or in combination. The reaction temperature ranges from −30° C. to 100° C., preferably 0° C. to 30° C., while the reaction time is 0.1 to 100 hours, preferably 1 to 20 hours. In a case where the pyrimidine nucleoside derivative represented by formula (2) has a protecting group(s) on its nitrogen atom(s), a deprotecting reagent may be reacted to remove the protecting group(s) to thereby obtain a compound represented by formula (1), according to the procedures shown in Scheme 1.

The compound of formula (2) or (1) as obtained above according to Scheme 1 or 2 can form a salt, especially a pharmaceutically acceptable salt, in a generally known manner. Examples of a pharmaceutically acceptable salt include salts with mineral acids such as hydrochloric acid, hydrobromic acid, sulfuric acid, nitric acid and phosphoric acid, as well as salts with organic acids such as trifluoroacetic acid, acetic acid, propionic acid, formic acid, methanesulfonic acid and paratoluenesulfonic acid. The compound of formula (1) or (2) or a salt thereof can be isolated and purified using generally known separation/purification means, such as concentration, solvent extraction, filtration, recrystallization, and/or various chromatographic techniques.

For use as a pharmaceutical preparation, the compound of the present invention may be formulated into any dosage form as appropriate for prophylactic or therapeutic purposes. Examples of such a dosage form include oral formulations, injections, suppositories, creams and plasters, with creams being preferred for use. These dosage forms may each be prepared by conventional formulation techniques well known to those skilled in the art.

In the case of preparing solid formulations for oral administration, the compound of the present invention may be supplemented with excipients and, if necessary, with binders, disintegrating agents, lubricants, coloring agents, correctives and so on, followed by formulating in a routine manner into tablets, coated tablets, granules, powders, capsules, etc. Such additives may be those commonly used in the art, as exemplified by lactose, sucrose, sodium chloride, glucose, starch, calcium carbonate, kaolin, microcrystalline cellulose and silicate for excipients; water, ethanol, propanol, simple syrup, glucose solution, starch solution, gelatin solution, carboxymethylcellulose, hydroxypropylcellulose, hydroxypropylstarch, methylcellulose, ethylcellulose, shellac, calcium phosphate and polyvinylpyrrolidone for binders; dry starch, sodium alginate, agar powder, sodium bicarbonate, calcium carbonate, sodium lauryl sulfate, stearic acid monoglyceride and lactose for disintegrating agents; purified talc, stearate salt, borax and polyethylene glycol for lubricants; titanium oxide and iron oxide for coloring agents; and sucrose, orange peel, citric acid and tartaric acid for correctives.

In the case of preparing liquid formulations for oral administration, the compound of the present invention may be supplemented with correctives, buffers, stabilizers and so on, followed by formulating in a routine manner into oral solutions, syrups, elixirs, etc. In this case, correctives may be those listed above. Examples of buffers include sodium citrate, while examples of stabilizers include tragacanth, gum arabic and gelatin.

In the case of preparing injections, the compound of the present invention may be supplemented with pH adjustors, buffers, stabilizers, isotonizing agents, local anesthetic agents and so on, followed by formulating in a routine manner into subcutaneous, intramuscular and intravenous injections. In this case, examples of pH adjustors and buffers include sodium citrate, sodium acetate, and sodium phosphate. Likewise, examples of stabilizers include sodium pyrosulfite, EDTA, thioglycolic acid, and thiolactic acid. Examples of local anesthetic agents include procaine hydrochloride and lidocaine hydrochloride. Examples of isotonizing agents include sodium chloride and glucose.

In the case of preparing suppositories, the compound of the present invention may be supplemented with pharmaceutical carriers known in the art (e.g., polyethylene glycol, lanolin, cacao butter, fatty acid triglyceride) and, if necessary, with additional ingredients such as surfactants (e.g., Tween (registered trademark)), followed by formulating in a routine manner.

In the case of preparing creams, the compound of the present invention may be combined with commonly used base materials, stabilizers, wetting agents, preservatives and so on, as appropriate for the intended purpose, followed by mixing and formulating in a routine manner. Examples of base materials include liquid paraffin, white petrolatum, white beeswax, octyldodecyl alcohol, and paraffin. Examples of preservatives include methyl parahydroxybenzoate, ethyl parahydroxybenzoate, and propyl parahydroxybenzoate.

In the case of preparing plasters, the above creams, ointments, gels, pastes or the like may be applied onto commonly used supports in a routine manner. Suitable supports are woven or nonwoven fabrics made of cotton, staple fibers or chemical fibers, as well as films or foamed sheets made of soft vinyl chloride, polyethylene, polyurethane, etc.

The amount of the compound of the present invention to be incorporated into the above dosage unit forms will vary depending on the symptom of a patient to be applied by the compound, or depending on the intended dosage form, etc. A desired amount per dosage unit form is usually about 1 to 1000 mg for oral formulations, about 0.1 to 500 mg for injections, and about 5 to 1000 mg for suppositories. Moreover, the daily dose of pharmaceutical agents having the above dosage forms will vary depending on, e.g., the symptom, body weight, age and sex of a patient, and hence should be determined for each case. However, the daily dose may generally be set to about 0.1 to 5000 mg, preferably 1 to 1000 mg per day for adult patients, preferably given as a single dose or in 2 to 4 divided doses per day.

Diseases which can be treated by administration of a pharmaceutical agent containing the compound of the present invention are human herpes infections, i.e., herpes simplex type 1 and 2 infections (HSV-1 and HSV-2 infections) including gingivostomatitis, keratitis, pharyngitis, herpes labialis, herpes encephalitis and genital herpes, as well as varicella and herpes zoster (VZV infections), EB virus infections such as infectious mononucleosis, etc.

EXAMPLES

The present invention will be further described in more detail by way of the following reference example, examples, pharmacological test examples and formulation examples, which are not intended to limit the scope of the invention.

Reference Example 1

Synthesis of 1-β-D-arabinofuranosyl-(E)-5-(2-chlorovinyl)uracil (CVAU)

This compound was synthesized according to synthesis procedures as described in JP 57-48160 B or other documents.

Example 1

Synthesis of (E)-5-(2-chlorovinyl)-1-[5'-O-(piperidine-4-carboxyl)-β-D-arabinofuranosyl]uracil hydrochloride (Compound 1)

To a solution of 1-β-D-arabinofuranosyl-(E)-5-(2-chlorovinyl)uracil (CVAU; 20.0 g), (N-Boc)piperidine-4-carboxylic acid (15.2 g), HOBT monohydrate (11.1 g) and triethylamine (7.3 g) in DMF (180 ml), EDC (11.2 g) was added dropwise at −6° C. to −3° C. After completion of the dropwise addition, the reaction mixture was stirred overnight at room temperature. The DMF was distilled off under reduced pressure, and the resulting residue was dissolved in ethyl acetate (100 ml) and then washed with 5% aqueous sodium bicarbonate and saturated aqueous sodium chloride.

After drying over anhydrous magnesium sulfate, the ethyl acetate was distilled off under reduced pressure to give a light-yellow oil (33.6 g). This oil was crystallized from n-hexane and collected by filtration to give a crude product (13.6 g). This procedure was repeated twice.

The crude product thus obtained (17.1 g) was dissolved without purification in dioxane (50 ml), and a 4 N hydrogen chloride/dioxane solution (83 ml) was added dropwise thereto under ice cooling. After completion of the dropwise addition, the reaction mixture was stirred overnight at room temperature. The dioxane was distilled off under reduced pressure, and the resulting opalescent crystal (14.4 g) was washed by suspending in dioxane and ethanol, followed by filtration to give Compound 1 (12.8 g).

[Formula 3]

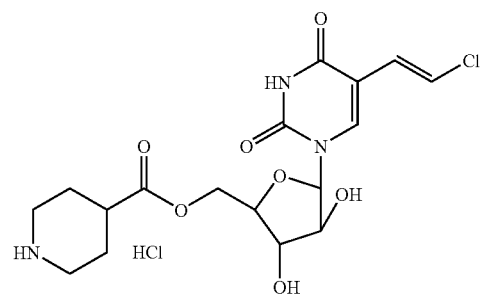

$^1$H-NMR (DMSO-d$_6$) δ 11.63 (1H, s), 8.89 (1H, br), 8.60 (1H, br), 7.65 (1H, s), 7.21 (1H, d, J=13.17 Hz), 6.66 (1H, d, J=13.17 Hz), 6.06 (1H, d, J=3.90 Hz), 5.76 (1H, d, J=4.39 Hz), 5.70 (1H, d, J=3.90 Hz), 4.58 (1H, dd, J=11.71 Hz, J=8.29 Hz), 4.22 (1H, dd, J=11.71 Hz, J=3.42 Hz), 4.03-3.95 (3H, m), 3.23-3.21 (2H, m), 2.94-2.91 (2H, m), 2.02-1.99 (2H, m), 1.80-1.74 (2H, m)

MS (FAB): m/z 450

Example 2

Synthesis of 1-[5'-0-(L-valine)-β-D-arabinofuranosyl]-(E)-5-(2-chlorovinyl)uracil hydrochloride (Compound 2)

To a solution of CVAU (20.0 g), Boc-L-valine (14.4 g), HOBT monohydrate (11.1 g) and triethylamine (7.3 g) in DMF (200 ml), EDC (11.2 g) was added dropwise at −6° C. to −3° C. After completion of the dropwise addition, the reaction mixture was stirred overnight at room temperature. The DMF was distilled off under reduced pressure, and the resulting residue was dissolved in ethyl acetate (100 ml) and then washed with 5% aqueous sodium bicarbonate and saturated aqueous sodium chloride. After drying over anhydrous magnesium sulfate, the ethyl acetate was distilled off under reduced pressure to give a light-yellow oil (37.6 g). This oil was crystallized from n-hexane and chloroform, followed by filtration to give a crude product (13.5 g). The crude product thus obtained (13.5 g) was dissolved without purification in dioxane (130 ml), and a 4 N hydrogen chloride/dioxane solution (67 ml) was added dropwise thereto under ice cooling. After completion of the dropwise addition, the reaction mixture was stirred overnight at room temperature. The dioxane was distilled off under reduced pressure, and the resulting residue was crystallized from ether and collected by filtration to give Compound 2 (12.9 g).

[Formula 4]

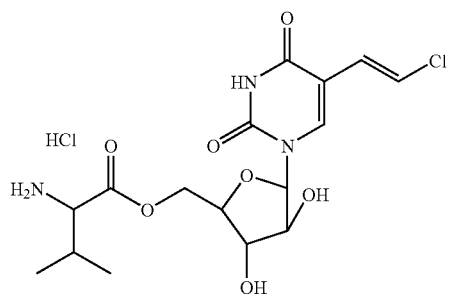

$^1$H-NMR (DMSO-d$_6$) δ 11.66 (1H, s), 8.37 (3H, brs), 7.64 (1H, s), 7.23 (1H, d, J=13.17 Hz), 6.63 (1H, d, J=13.17 Hz), 6.08 (1H, d, J=3.90 Hz), 5.79 (1H, d, J=4.63 Hz), 5.72 (1H, d, J=3.90 Hz), 4.65 (1H, dd, J=11.71 Hz, J=8.54 Hz), 4.39-4.35 (1H, m), 4.05-3.99 (4H, m), 2.20-2.16 (1H, m), 1.00 (3H, d, J=6.83 Hz), 0.96 (3H, d, J=6.83 Hz)

MS (FAB): m/z 438

Example 3

Synthesis of (E)-5-(2-chlorovinyl)-1-[5'-O-(pyridine-3-carboxyl)-β-D-arabinofuranosyl]uracil hydrochloride (Compound 3)

CVAU (500 mg) was dissolved in DMF (4 ml). To this solution, nicotinoyl chloride hydrochloride (427 mg) and triethylamine (648 mg) were added at room temperature and stirred for 3 hours. Nicotinoyl chloride hydrochloride (114 mg) and triethylamine (80 mg) were further added and stirred for an additional 2 hours. After addition of methanol to stop the reaction, ethyl acetate was added. The organic layer was washed with saturated aqueous sodium bicarbonate and then with water, followed by evaporation to dryness under reduced pressure. The residue was crystallized from methanol-chloroform to give a crude product (100 mg).

The crude product (70 mg) was dissolved in a 10% hydrochloric acid/methanol solution, and the methanol was evaporated to dryness under reduced pressure to give Compound 3 (80 mg).

[Formula 5]

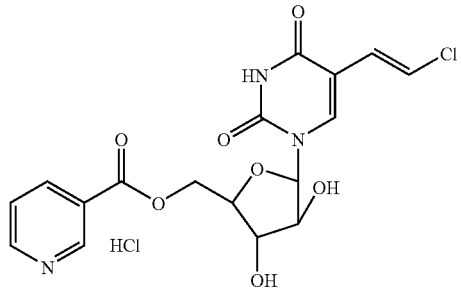

$^1$H-NMR (DMSO-d$_6$) δ 11.60 (s, 1H), 9.16 (m, 1H), 8.86 (dd, 1H, J=5.0, 1.7 Hz), 8.41 (dt, 1H, J=8.0, 2.0 Hz), 7.65 (m, 1H), 7.65 (s, 1H), 7.15 (d, 1H, J=13.2 Hz), 6.53 (d, 1H, J=13.2 Hz), 6.07 (d, 1H, J=3.6 Hz), 4.73 (dd, 1H, J=11.5 Hz, J=7.3 Hz), 4.53 (dd, 1H, J=11.5 Hz, J=3.6 Hz), 4.07 (m, 3H)

MS (FAB): m/z 410

Example 4

Synthesis of (E)-5-(2-chlorovinyl)-1-[5'-O-(pyridine-4-carboxyl)-β-D-arabinofuranosyl]uracil hydrochloride (Compound 4)

Isonicotinic acid (689 mg), isobutyl chloroformate (764 mg) and triethylamine (566 mg) were dissolved in DMF (8 ml) and stirred for 1 hour. To the reaction mixture, CVAU (1.0 g) and triethylamine (1.0 g) were added and stirred overnight. After addition of methanol to stop the reaction, ethyl acetate was added. The organic layer was washed with saturated aqueous sodium bicarbonate and then with saturated aqueous sodium chloride, followed by evaporation to dryness under reduced pressure. The residue was crystallized from methanol-chloroform to give a crude product (220 mg).

The crude product (70 mg) was dissolved in a 10% hydrochloric acid/methanol solution, and the methanol was evaporated to dryness under reduced pressure, followed by crystallization from methanol to give Compound 4 (80 mg).

[Formula 6]

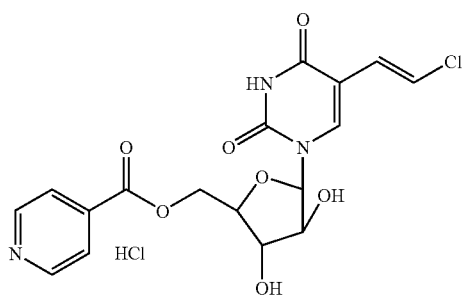

¹H-NMR (DMSO-d₆) δ 11.60 (s, 1H), 8.90 (dd, 2H, J=4.6, 1.7 Hz), 8.04 (dd, 2H, J=4.6, 1.7 Hz), 7.67 (s, 1H), 7.16 (d, 1H, J=13.2 Hz), 6.58 (d, 1H, J=13.2 Hz), 6.07 (d, 1H, J=3.3 Hz), 4.75 (dd, 1H, J=11.9 Hz, J=7.3 Hz), 4.65 (dd, 1H, J=11.9 Hz, J=3.6 Hz), 4.11 (m, 3H)

MS (FAB): m/z 410

Example 5

Synthesis of (E)-5-(2-chlorovinyl)-1-[5'-O—(N-methylpiperidine-4-carboxyl)-β-D-arabinofuranosyl]uracil hydrochloride (Compound 5)

N-Methylisonipecotic acid sodium salt (1.5 g) in DMF (14 ml) was treated with 1 N hydrochloric acid (9.1 ml) and dried to give a white solid. This solid was dissolved in isobutyl chloroformate (1.24 g) and triethylamine (1.0 g), followed by stirring for 1 hour. To the reaction mixture, CVAU (1.3 g) and triethylamine (2.7 g) were added and stirred overnight. After addition of methanol to stop the reaction, ethyl acetate was added. The organic layer was washed with saturated aqueous sodium bicarbonate and then with saturated aqueous sodium chloride, followed by evaporation to dryness under reduced pressure. The residue was purified by NH silica gel column chromatography (chloroform:methanol=7:1) to give a crude product. The crude product was immediately treated with a large excess of a 10% hydrochloric acid/methanol solution to give a crude hydrochloride salt. This crude product was suspended in ethyl acetate, and the organic layer was washed with saturated aqueous sodium bicarbonate and evaporated to dryness under reduced pressure. The resulting residue was purified again by NH silica gel column chromatography (chloroform:methanol=7:1), treated with about 2 molar equivalents of a 10% hydrochloric acid/methanol solution, and then lyophilized to give Compound 5 (182 mg).

[Formula 7]

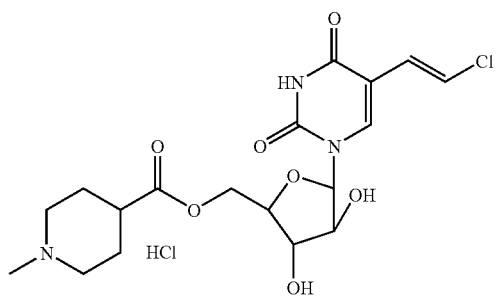

¹H-NMR (DMSO-d₆) δ 11.60 (s, 1H), 7.63 (s, 1H), 7.20 (d, 1H, J=13.3 Hz), 6.64 (d, 1H, J=13.3 Hz), 6.04 (d, 1H, J=4.3 Hz), 5.72, 5.66 (each d, each 1H J=4.3, 3.6 Hz), 4.54 (dd, 1H, J=11.5 Hz, J=7.6 Hz), 4.19 (dd, 1H, J=11.4 Hz, J=3.0 Hz), 3.97 (m, 3H), 3.33-1.71 (m, 9H), 2.46 (s, 3H)

MS (FAB): m/z 430

Example 6

Synthesis of (E)-5-(2-chlorovinyl)-1-[5'-O-(pyridine-2-carboxyl)-β-D-arabinofuranosyl]uracil (Compound 6)

CVAU (500 mg) was dissolved in DMF (4 ml). To this solution, picolinoyl chloride hydrochloride (427 mg) and triethylamine (647 mg) were added at room temperature and stirred for 3 hours. Nicotinoyl chloride hydrochloride (114 mg) and triethylamine (80 mg) were further added and stirred for an additional 2 hours. After addition of methanol to stop the reaction, ethyl acetate was added. The organic layer was washed with saturated aqueous sodium bicarbonate and then with water, followed by evaporation to dryness under reduced pressure. The residue was crystallized from methanol-chloroform to give Compound 6 (220 mg).

[Formula 8]

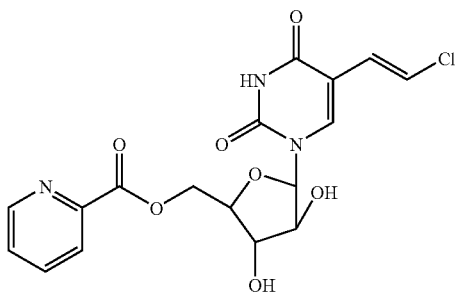

¹H-NMR (DMSO-d₆) δ 11.56 (s, 1H), 8.74 (d, 1H, J=4.0 Hz), 8.10 (d, 1H, J=8.0 Hz), 8.01 (dt, 1H, J=7.6, 1.7 Hz), 7.70 (s, 1H), 7.67 (m, 1H), 7.19 (d, 1H, J=13.2 Hz), 6.57 (d, 1H, J=13.2 Hz), 6.08 (d, 1H, J=4.0 Hz), 5.73, 5.69 (each d, each 1H J=4.6, 4.0 Hz), 4.73 (dd, 1H, J=11.9 Hz, J=7.3 Hz), 4.52 (dd, 1H, J=11.9 Hz, J=3.6 Hz), 4.08 (m, 3H)

MS (FAB): m/z 410

Example 7

Synthesis of (E)-5-(2-chlorovinyl)-1-[5'-O-(2-methoxypyrimidin-5-yl-carboxyl)-β-D-arabinofuranosyl]uracil (Compound 7)

2-Methoxypyrimidine-5-carboxylic acid (688 mg), isobutyl chloroformate (610 mg) and triethylamine (452 mg) were dissolved in DMF (7 ml) and stirred for 1 hour. To the reaction mixture, CVAU (1.0 g) and triethylamine (730 mg) were added and stirred overnight. After addition of methanol to stop the reaction, ethyl acetate was added. The organic layer was washed with saturated aqueous sodium bicarbonate and then with saturated aqueous sodium chloride, followed by evaporation to dryness under reduced pressure. The residue was crystallized from methanol-chloroform to give Compound 7 (180 mg).

[Formula 9]

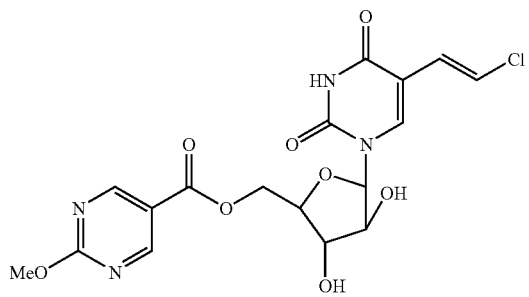

$^1$H-NMR (DMSO-$d_6$) δ 11.59 (s, 1H), 9.10 (s, 2H), 7.66 (s, 1H), 7.14 (d, 1H, J=13.2 Hz), 6.53 (d, 1H, J=13.2 Hz), 6.05 (d, 1H, J=4.0 Hz), 5.72, 5.68 (each d, each 1H, J=4.6, 4.0 Hz), 4.68 (dd, 1H, J=6.9 Hz, J=11.5 Hz), 4.51 (dd, 1H, J=3.3 Hz, J=11.5 Hz), 4.08 (m, 3H), 4.01 (s, 3H)

MS (FAB): m/z 441

Pharmacological Test Example 1

In Vitro Antiviral Test

The compounds of the present invention were measured for their in vitro antiviral activity (anti-HSV-1 activity, anti-VZV activity) by using human fetal lung-derived cells in an assay for 50% plaque formation inhibition (Japanese Journal of Chemotherapy, Vol. 38, No. 3, 256-261, 1990). As a result, as shown in Table 1, the compounds of the present invention showed in vitro antiviral activity almost comparable to that of CVAU and were found to have an antiviral effect on HSV-1 and VZV.

TABLE 1

In vitro anti-HSV-1 and anti-VZV activity of CVAU derivatives

| Compound | Anti-HSV-1 activity (ED50$^a$) μM | Anti-VZV activity (ED50) μM |
| --- | --- | --- |
| CVAU | 0.075 | 0.0089 |
| Compound 1 | 0.40 | 0.046 |
| Compound 2 | 0.12 | 0.019 |
| Compound 3 | 0.49 | 0.052 |
| Compound 4 | 0.13 | 0.021 |
| Compound 5 | 0.56 | 0.047 |

$^a$effective concentration required to reduce the number of plaques to 50%

Pharmacological Test Example 2

In Vivo Antiviral Test

Creams were prepared for the compounds of the present invention according to Formulation Example 2 and tested for their therapeutic effect on HSV-1 infection in mouse skin. The incidence rate and survival rate in each treated group are shown in Table 2. Moreover, skin symptoms in the HSV-1-infected mice were scored (Antiviral Research, 17, 133-143, 1992), and the time course of changes in their average lesion scores is shown in FIG. 1. When compared to the control group treated with no drug, Compound 1 was found to reduce the incidence rate, and showed a significant increase in the survival rate and a reduction in the lesion score. Compound 2 also showed a significant increase in the survival rate and a reduction in the lesion score. These results indicated that these compounds also had an excellent in vivo antiviral effect.

TABLE 2

Therapeutic effect of CVAU derivatives in HSV-1 mouse skin infection model

| Drug | Incidence rate | Survival rate | Mean survival days (Mean ± SE) |
| --- | --- | --- | --- |
| Control | 8/8 | 0/8 | 6.9 ± 0.12 |
| Compound 1 | 4/8 | 7/8 P < 0.01$^a$ | |
| Compound 2 | 8/8 | 7/8 P < 0.01 | |
| CVAU | 6/8 | 7/8 P < 0.01 | |

$^a$chi-square test (Yates' correction)

Formulation Example 1

Tablets

Compound 150 mg
Corn starch 50 mg
Microcrystalline cellulose 50 mg
Hydroxypropylcellulose 15 mg
Lactose 47 mg
Talc 2 mg
Magnesium stearate 2 mg
Ethylcellulose 30 mg
Unsaturated glyceride 2 mg
Titanium dioxide 2 mg According to the combination ratio indicated above, tablets (250 mg per tablet) were prepared in a routine manner.

Formulation Example 2

Creams

Compound 23.92 mg
POE (5) glyceryl monostearate 5.0 mg
Dimethylpolysiloxane 0.3 mg
セタール 1.5 mg
Paraffin 5.0 mg
White petrolatum 9.0 mg
Glyceryl monostearate 0.5 mg
Propylene glycol 20 mg
Adjusted to 100 mg with purified water.

According to the ratio indicated above, creams were prepared in a routine manner and provided for Pharmacological Test Example 2.

Formulation Example 3

Granules

Compound 3300 mg
Lactose 540 mg
Corn starch 100 mg
Hydroxypropylcellulose 50 mg
Talc 10 mg According to the combination ratio indicated above, granules (1000 mg per package) were prepared in a routine manner.

Formulation Example 4

Capsules

Compound 4 100 mg
Lactose 30 mg
Corn starch 50 mg
Microcrystalline cellulose 10 mg
Magnesium stearate 3 mg According to the combination ratio indicated above, capsules (193 mg per capsule) were prepared in a routine manner.

Formulation Example 5

Injections

Compound 5 100 mg
Sodium chloride 3.5 mg
Injectable distilled water q.s.
(2 ml per ampule)

According to the combination ratio indicated above, injections were prepared in a routine manner.

Formulation Example 6

Syrups

Compound 6 200 mg
Purified sucrose 60 g
Ethyl parahydroxybenzoate 5 mg
Butyl parahydroxybenzoate 5 mg
Flavorings q.s.
Colorants q.s.
Purified water q.s.

According to the combination ratio indicated above, syrups were prepared in a routine manner.

Formulation Example 7

Suppositories

Compound 7 300 mg
Witepsol W-35 1400 mg
(registered trademark, a mixture of mono-, di- and tri-glycerides of saturated fatty acids ranging from lauric acid to stearic acid, Dynamit Nobel)

According to the combination ratio indicated above, suppositories were prepared in a routine manner.

INDUSTRIAL APPLICABILITY

The novel pyrimidine nucleoside derivatives of the present invention and salts thereof are highly effective in in vivo tests, and hence can be expected to be used as antiviral agents (therapeutic agents for virus infections).

The invention claimed is:

1. A pyrimidine nucleoside represented by the following formula (I) or a salt thereof:

(1)

wherein R represents a nitrogen-containing heterocyclic ring which may have any one of a $C_1$-$C_3$ alkyl group or a $C_1$-$C_3$ alkoxy group as a substituent, or a $C_1$-$C_6$ alkyl group which has one primary amino group as a substituent.

2. The pyrimidine nucleoside or salt thereof according to claim 1, wherein R is a piperidyl group which may have a $C_1$-$C_3$ alkyl group as a substituent, a pyridyl group which may have a $C_1$-$C_3$ alkyl group as a substituent, or a pyrimidinyl group which may have a $C_1$-$C_3$ alkoxy group as a substituent.

3. The pyrimidine nucleoside or salt thereof according to claim 1, wherein R is a 4-piperidyl group.

4. The pyrimidine nucleoside or salt thereof according to claim 1, wherein R is a 1-amino-2-methyl-propyl group.

5. An antiviral agent comprising the pyrimidine nucleoside or salt thereof according to claim 1, as an active ingredient.

6. An antiviral agent comprising the pyrimidine nucleoside or salt thereof according to claim 2, as an active ingredient.

7. An antiviral agent comprising the pyrimidine nucleoside or salt thereof according to claim 3 as an active ingredient.

8. An antiviral agent comprising the pyrimidine nucleoside or salt thereof according to claim 4 as an active ingredient.

9. The antiviral agent according to claim 5, which is used as a therapeutic agent for a herpes virus infection.

10. The antiviral agent according to claim 6, which is used as a therapeutic agent for a herpes virus infection.

11. The antiviral agent according to claim 7, which is used as a therapeutic agent for a herpes virus infection.

12. The antiviral agent according to claim 8, which is used as a therapeutic agent for a herpes virus infection.

13. A method for treating a herpes virus infection selected from HSV-1 and VZV, which comprises administering a therapeutically effective amount of at least one pyrimidine nucleoside represented by the following formula (1) or salt thereof to a patient in need of treatmet:

(1)

wherein R represents a nitrogen-containing heterocyclic ring which may have any one of a $C_1$-$C_3$ alkyl group or a $C_1$-$C_3$ alkoxy group as a substituent, or a $C_1$-$C_6$ alkyl group which has one primary amino group as a substituent.

* * * * *